(12) United States Patent
Ramani et al.

(10) Patent No.: US 11,334,198 B2
(45) Date of Patent: *May 17, 2022

(54) FLEXIBLE TOUCH SENSING SYSTEM AND METHOD

(71) Applicant: Purdue Research Foundation, West Lafayette, IN (US)

(72) Inventors: Karthik Ramani, West Lafayette, IN (US); Sang Ho Yoon, Redmond, WA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/614,729

(22) PCT Filed: May 18, 2018

(86) PCT No.: PCT/US2018/033556
§ 371 (c)(1),
(2) Date: Nov. 18, 2019

(87) PCT Pub. No.: WO2018/213816
PCT Pub. Date: Nov. 22, 2018

(65) Prior Publication Data
US 2020/0183514 A1 Jun. 11, 2020

Related U.S. Application Data

(60) Provisional application No. 62/508,122, filed on May 18, 2017.

(51) Int. Cl.
*G06F 3/045* (2006.01)
*G06F 3/044* (2006.01)
(Continued)

(52) U.S. Cl.
CPC ............ *G06F 3/044* (2013.01); *G06F 3/0416* (2013.01); *G06F 3/04166* (2019.05);
(Continued)

(58) Field of Classification Search
CPC ....... A61L 31/06; G06F 3/044; G06F 3/0416; G06F 2202/04102; G06F 2203/04103; G06T 11/003
(Continued)

(56) References Cited

U.S. PATENT DOCUMENTS 10,942,596 B2   3/2021 Harrison et al.
2009/0084674 A1 4/2009 Holzhacker et al.
(Continued)

OTHER PUBLICATIONS

A. Boyle et al. "Shape Deformation in Two-Dimensional Electrical Impedance Tomography," in IEEE Transactions on Medical Imaging, vol. 31, No. 12, pp. 2185-2193, Dec. 2012, doi: 10.1109/TMI.2012.2204438.
(Continued)

*Primary Examiner* — Abdul-Samad A Adediran
(74) *Attorney, Agent, or Firm* — Maginot, Moore & Beck LLP

(57) ABSTRACT

A single volume soft sensor capable of sensing real-time continuous contact and stretching. A low-cost and an easy method to fabricate such piezoresistive elastomer-based soft sensors for instant interactions is also provided. An electrical impedance tomography (EIT) technique is employed to estimate changes of resistance distribution on the sensor caused by fingertip contact. To compensate for the rebound elasticity of the elastomer and achieve real-time contact sensing, an adaptive baseline update for EIT is utilized. The baseline updates are triggered by fingertip contact and movement detections.

30 Claims, 16 Drawing Sheets

(51) Int. Cl.
*G06F 3/041* (2006.01)
*G06T 11/00* (2006.01)

(52) U.S. Cl.
CPC .. *G06T 11/003* (2013.01); *G06F 2203/04102* (2013.01); *G06F 2203/04103* (2013.01)

(58) Field of Classification Search
USPC .......................... 345/174; 700/258; 702/41
See application file for complete search history.

(56) References Cited

U.S. PATENT DOCUMENTS

| | | | |
|---|---|---|---|
| 2010/0049450 A1* | 2/2010 | Nagakubo | G01L 1/205 702/41 |
| 2010/0259503 A1* | 10/2010 | Yanase | G06F 3/04166 345/174 |
| 2012/0157827 A1 | 6/2012 | Ross et al. | |
| 2014/0365009 A1* | 12/2014 | Wettels | B25J 15/0028 700/258 |
| 2018/0116559 A1* | 5/2018 | Otaka | A61L 31/06 |
| 2020/0057531 A1 | 2/2020 | Yoon et al. | |

OTHER PUBLICATIONS

International Search Report corresponding to International Patent Application No. PCT/US2018/33556, dated Aug. 9, 2018 (2 pages).

\* cited by examiner

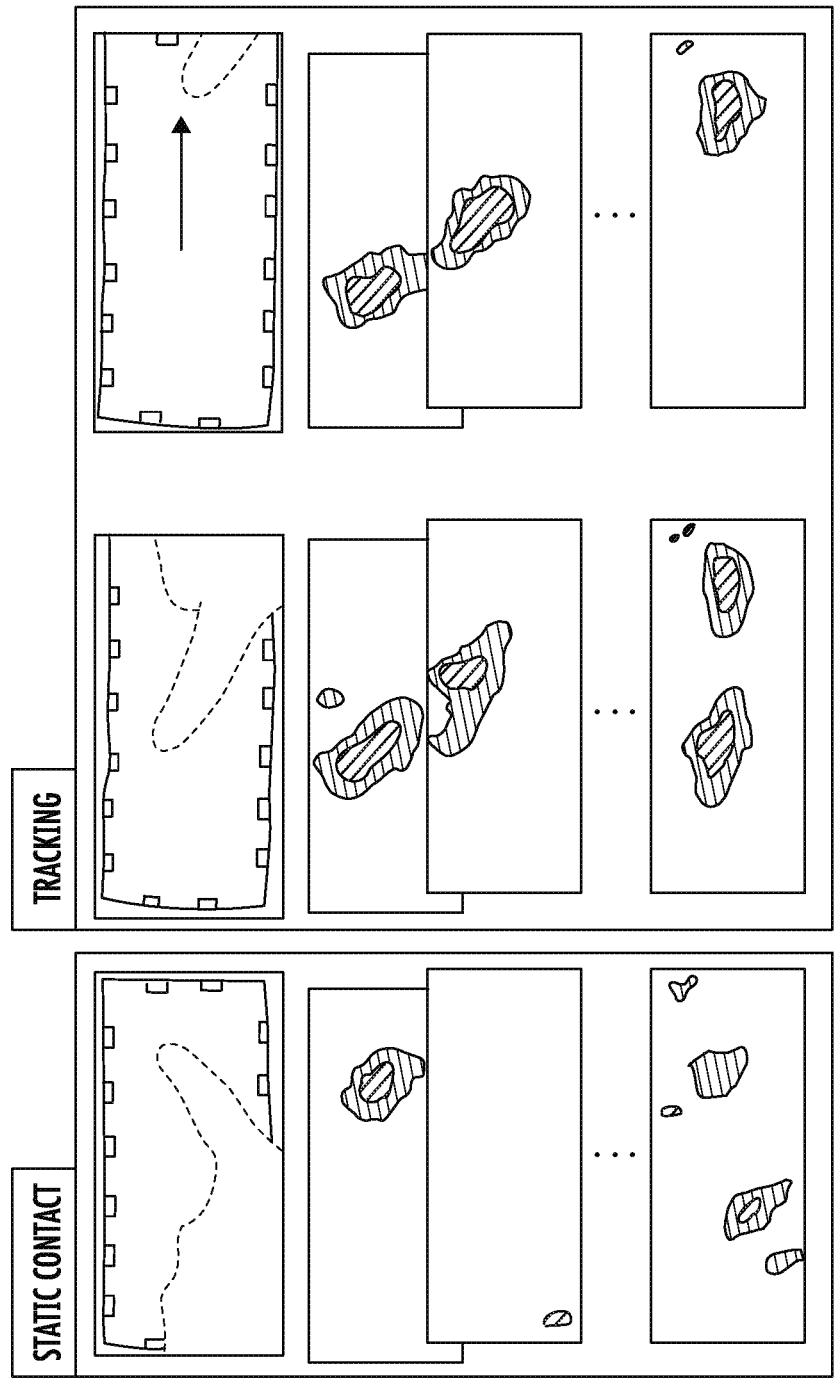

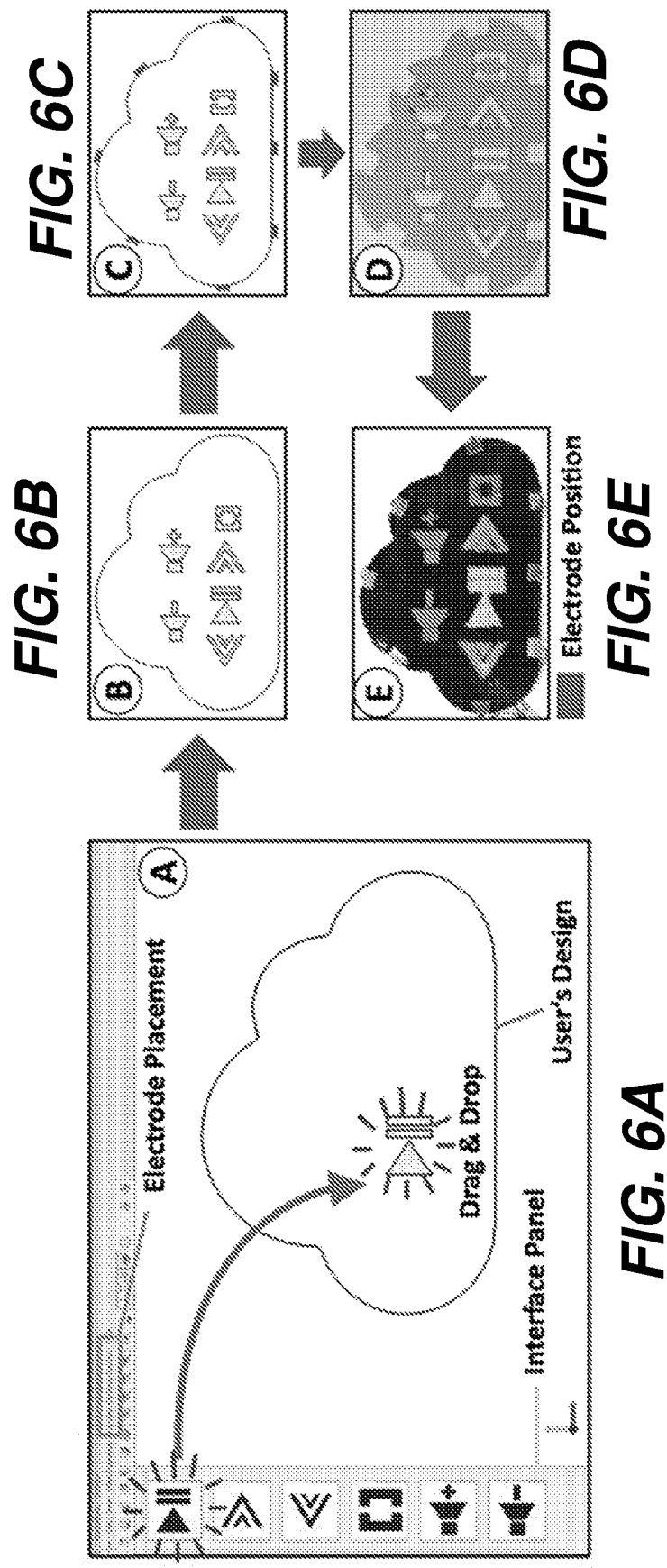

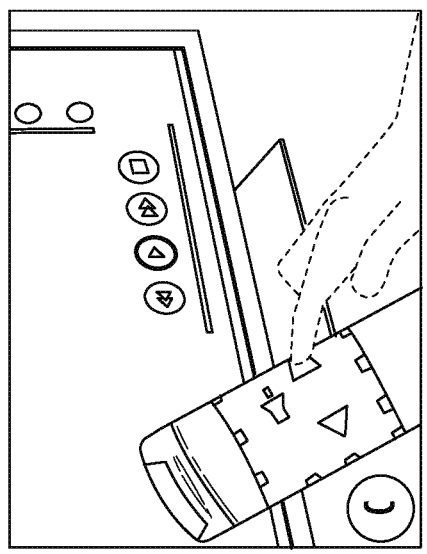
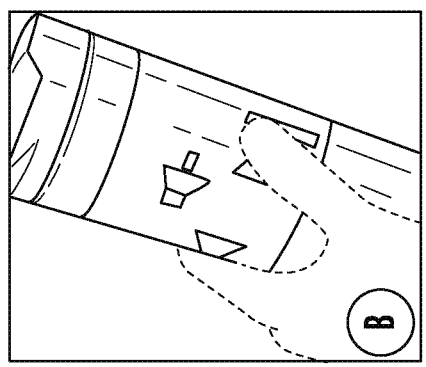
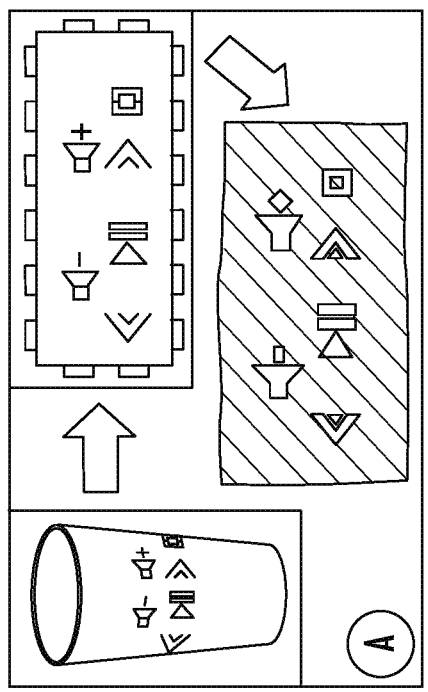
FIG. 11C
FIG. 11B
FIG. 11A

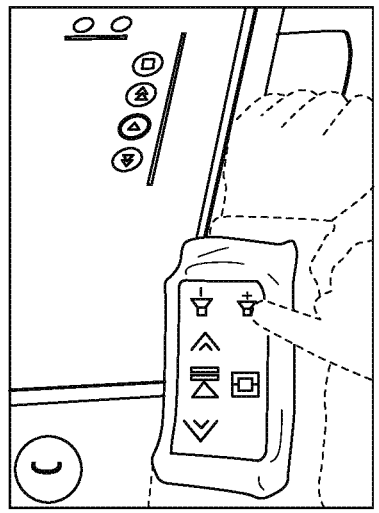
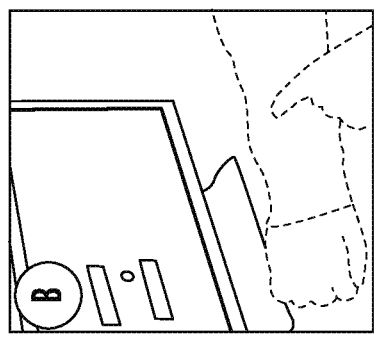
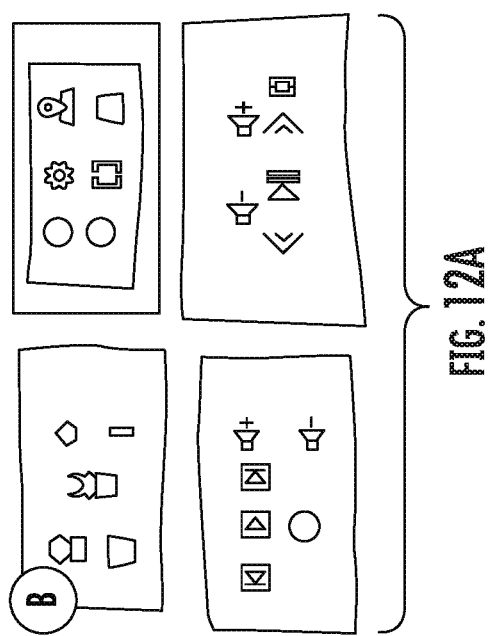
FIG. 12C
FIG. 12B
FIG. 12A

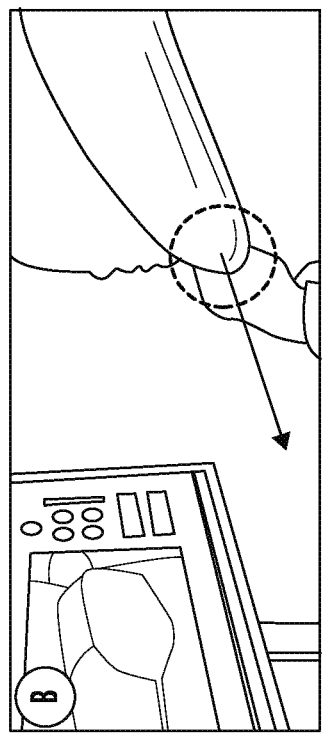
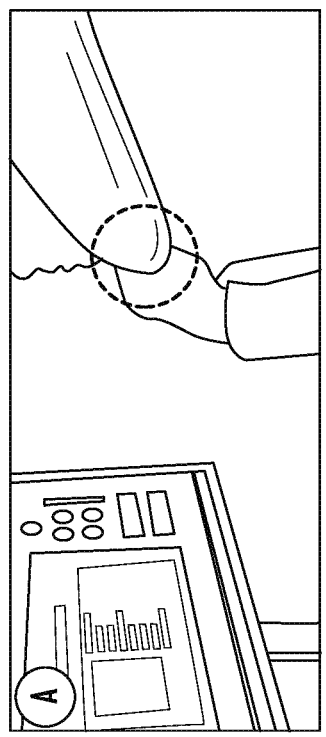

FLEXIBLE TOUCH SENSING SYSTEM AND METHOD

CROSS REFERENCE TO RELATED APPLICATION

This application claims priority to U.S. Provisional Patent Application No. 62/508,122 filed May 18, 2017, which is hereby incorporated by reference in its entirety.

BACKGROUND

Stretchable soft sensors have been explored as promising input methods for adding interactions on both rigid and elastic physical objects, smart textiles, shape-changing surfaces, humanoids, and the human body. With a high flexibility and stretchability of the sensors, a wide scope of natural applications have been suggested. Still, the expensive and multi-step fabrication processes hinder production of inexpensive, customized soft sensors.

SUMMARY

By jointly emphasizing fabrication, multi-modality and novel computational methods, the present disclosure provides a single-volume soft-matter sensor that provides multimodal sensing. The presently disclosed sensor and associated methods allow users to fabricate sensors inexpensively, customize interfaces easily, and deploy them instantly for continuous touch input.

In certain embodiments, the presently disclosed device utilizes carbon-filled liquid silicone rubber, a non-toxic piezoresistive material. The major hurdle in employing the carbon-filled silicone as an interaction input is the lack of real time sensing capability. This is mainly due to a rebound elasticity of the material, which causes a slow-recovery of the sensing signals after the material deformations that occur during an input event. In the present disclosure, an adaptive baseline update process is implemented using an electrical impedance tomography (EIT) process to achieve real-time contact localization. The disclosed system also utilizes stretching which enables multimodal sensing.

By employing the EIT technique, the presently disclosed system enables a human touch to interface and interact with the sensor via electrodes placed on the material boundary only. In this way, the sensor can be fabricated in a single-volume manner and implemented without invasive wirings or electronics or other elements which have to be fabricated and placed in the interior of the material boundary. No interior elements are required, instead the material itself is used as a sensor. Using the disclosed method provides sensing contact localization and stretching within the sensor material. To this end, users are allowed to perform interactions instantly after deployment without any extra training processes.

According to various aspects, a system is provided, comprising a single volume soft sensor capable of sensing real-time continuous contact and stretching. A low-cost and an easy way to fabricate such piezoresistive elastomer-based soft sensors for instant interactions is also provided. An electrical impedance tomography (EIT) technique is employed to estimate changes of resistance distribution on the sensor caused by fingertip contact. To compensate for the rebound elasticity of the elastomer and achieve real-time contact sensing, an adaptive baseline update for EIT is utilized. The baseline updates are triggered by fingertip contact and movement detections. Further, multimodal sensing with stretching using a linear regression model is also provided. A software toolkit for users to design and deploy personalized interfaces with customized sensors is also provided. Through a series of experiments and evaluations, the performance of discrete/continuous contact and stretching sensing is validated.

This summary is provided to introduce the selection of concepts in a form that is easy to understand the detailed embodiments of the descriptions. The embodiments are then brought together in a final embodiment which described an environment, thereby stressing that each of the embodiments may be viewed in isolation, but also the synergies among them are very significant. This summary is not intended to identify key subject matter or key features or essential features thereof.

BRIEF DESCRIPTION OF THE DRAWINGS

The above and other objects, features, and advantages of various examples will become more apparent when taken in conjunction with the following description and drawings wherein identical reference numerals have been used, where possible, to designate identical features that are common to the figures, and wherein:

FIG. 3A shows a continuous update touch event.

FIG. 3B shows a contact switch touch event.

FIG. 3C shows a contact+movement event.

FIG. 6A shows a toolkit interface.

FIG. 6B shows an interface customization.

FIG. 6C shows electrode placement.

FIG. 6D shows a guidance template.

FIG. 6E shows a resulting prototype sensor.

FIG. 11A shows an example sensor on a tumbler cup.

FIG. 11B shows the sensor of FIG. 11A in use.

FIG. 11C shows the sensor of FIG. 11A further in use.

FIG. 12A shows an example sensor on a user arm.

FIG. 12B shows the sensor of FIG. 12A in use.

FIG. 12C shows the sensor of FIG. 12A further in use.

FIG. 13A shows an example sensor on a neck pillow.

FIG. 13B shows the sensor of FIG. 13A in use.

DETAILED DESCRIPTION

The term "drawings" used herein refers to drawings attached herewith and to sketches, drawings, illustrations, photographs, or other visual representations found in this disclosure. The terms "I," "we," "our" and the like throughout this disclosure do not refer to any specific individual or group of individuals.

Figure 1A:
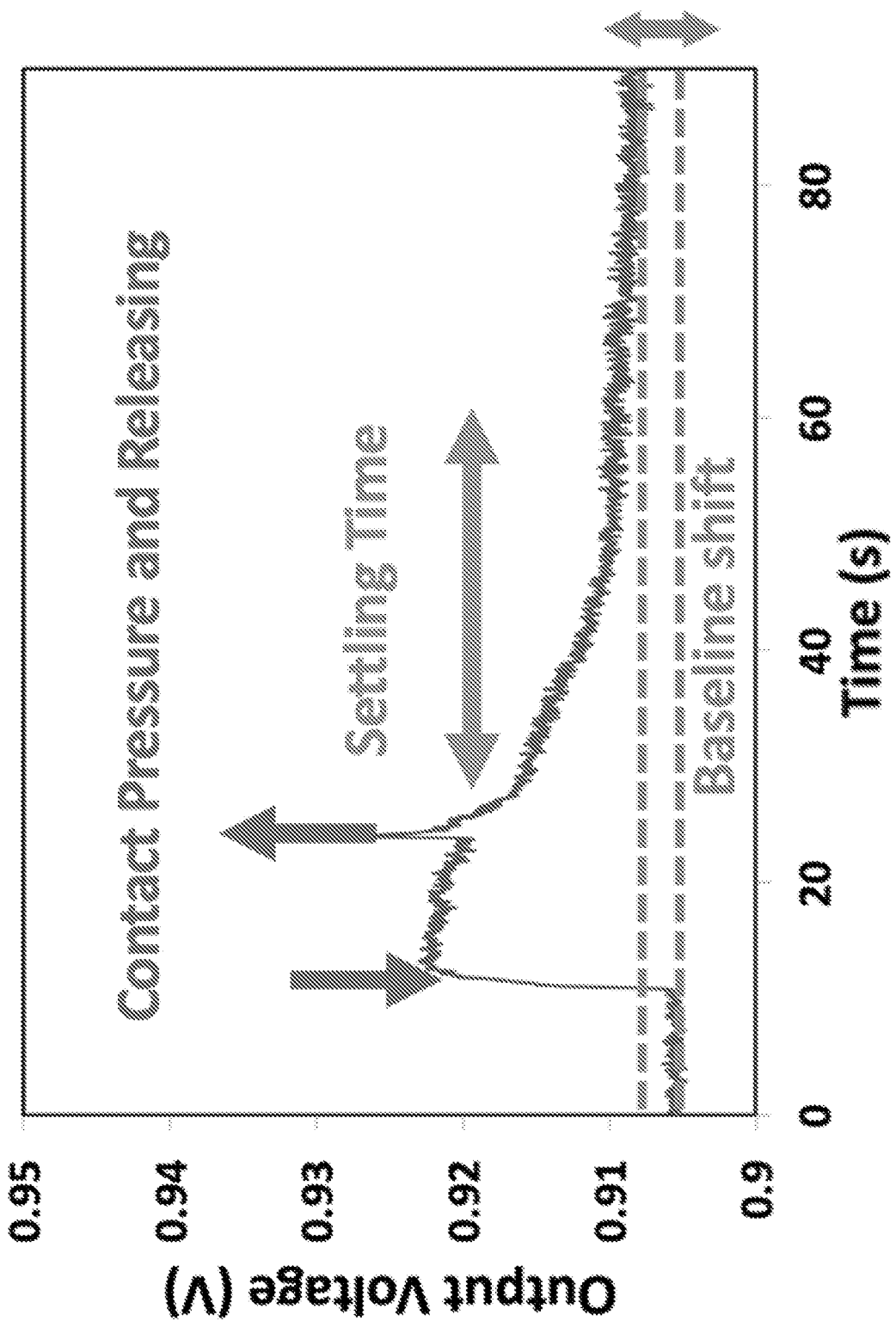
FIG. 1A illustrates voltage reading from a sensing channel fed with fixed DC current upon pressure.
Figure 1B:
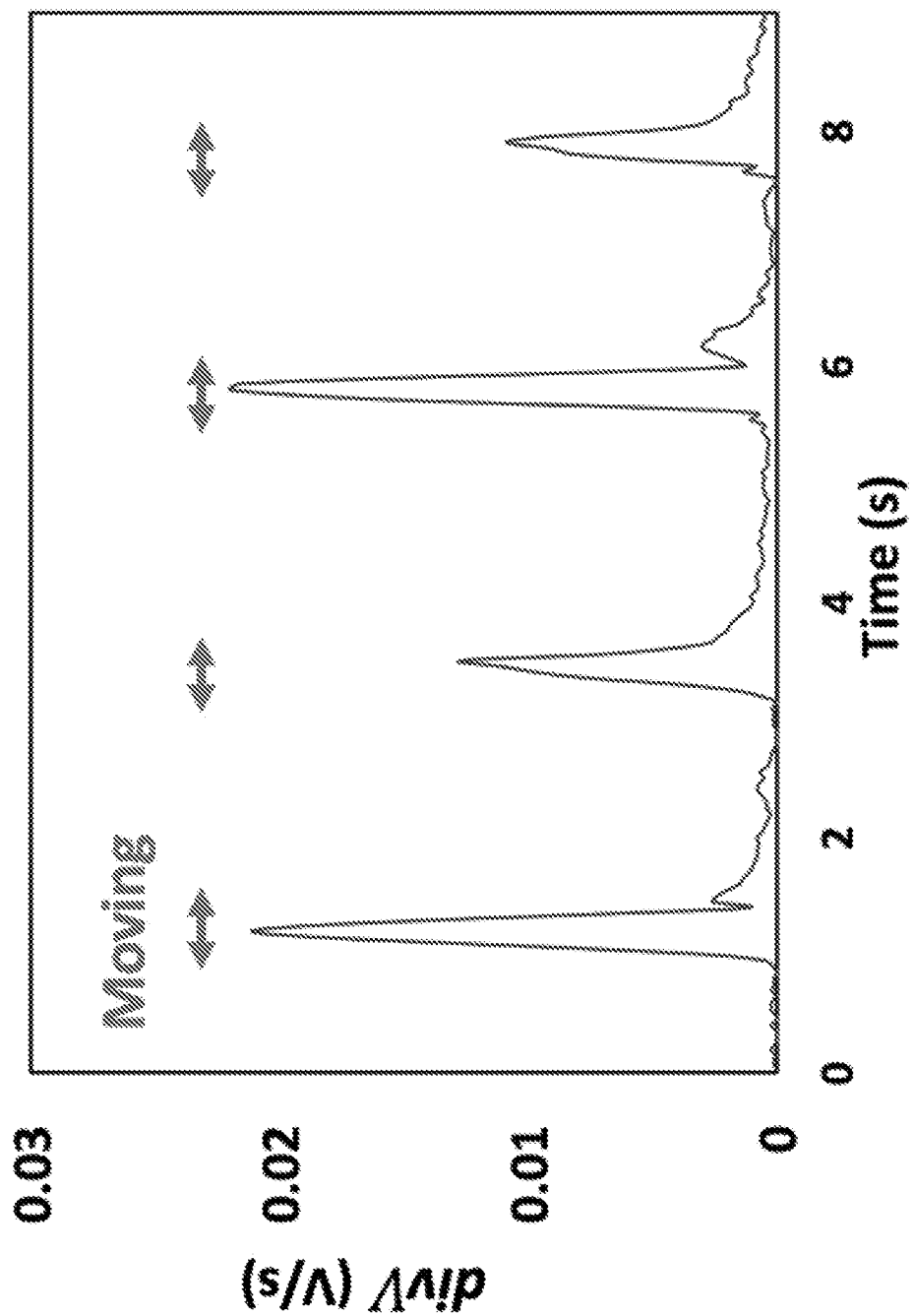
FIG. 1B illustrates movement detection using div $\nabla_i$ smoothed by a 5-frame running average.

Sensing performed by the presently disclosed system is based on an EIT technique which estimates the resistance distribution of the conductive material using inverse problem analysis based on measurements from the sensor boundary. The difficulty of providing real-time sensing with carbon-filled silicone rubber is due to the material's rebound elasticity (>50%), which causes a long settling time (>10 s) and small shifts in baseline values as shown in FIGS. 1A and 1B. FIG. 1A shows the voltage reading from a sensing channel fed with fixed DC current upon pressure. FIG. 1B shows movement detection using div $\overline{V}_i$ smoothed by a 5-frame running average.

Figure 2A:
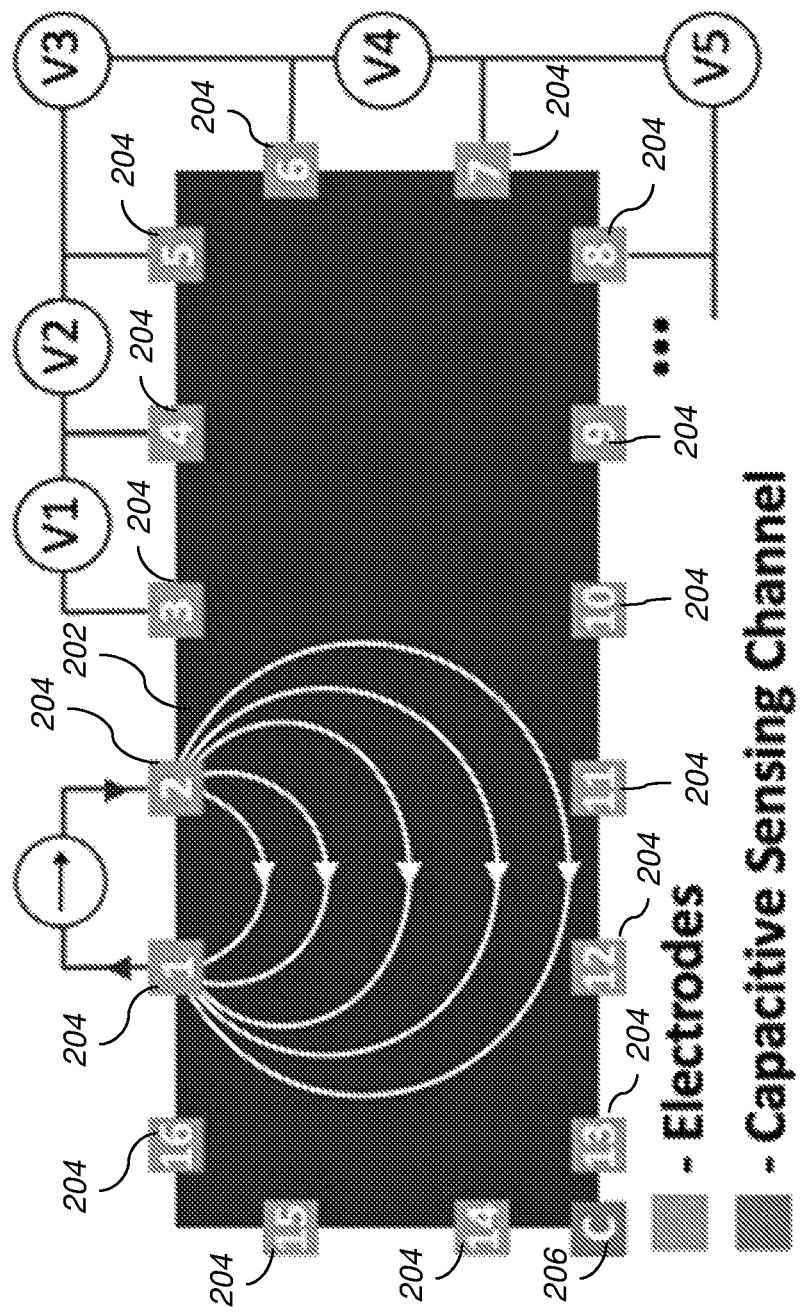
FIG. 2A illustrates a sensor activating the initial sensing electrode pair.
Figure 2B:
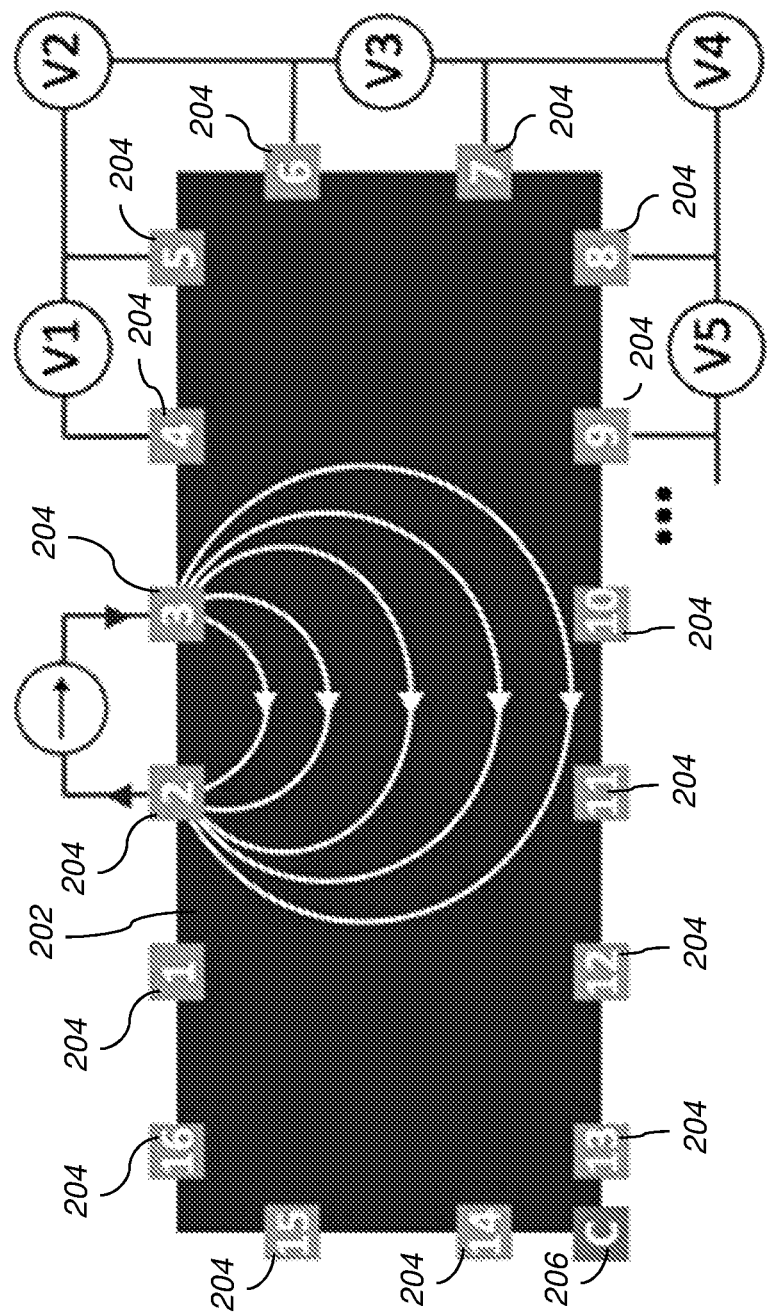
FIG. 2B illustrates a sensor activating a subsequent sensing electrode pair.

The presently disclosed sensing method is based on carbon-filled liquid silicone rubber that changes its resistance distribution upon mechanical deformations. In one example, four-terminal sensing is used to measure resistance since this method reduces the inaccuracy from contact resistances. Unlike matrix tactile sensors where arrays of electrodes are required within the sensing area, the presently disclosed system utilizes sensing electrodes 204 and a capacitive channel 206 coupled to the outer edge of the sensor 202. Then, a Neighboring Method is used where DC current is fed through two adjacent electrodes 202 and the voltage differential is measured successively throughout the adjacent electrode pairs as shown in FIGS. 2A and 2B. FIG. 2A shows the initial sensing electrode pair and FIG. 2B shows the next successive electrode pair sensing.

According to one embodiment, EIT image reconstruction is carried out by comparing the measurements at two different instances. Previous work showed discrete contact sensing using EIT with carbon elastomer by taking measurements under the initial no-load condition as a constant baseline. However, a small shift in the reference baseline can easily distort the contact localization. Thus, the use of a constant baseline will not perform accurately if baseline shifts. Furthermore, the long settling time limits the applicability in dynamic situations such as fast discrete contacts and continuous movement. In order to eliminate the distortion and apply EIT for real-time contact sensing, the presently disclosed system utilizes a dynamic baseline update method. The update method comprises the following three steps:

Continuous Update (FIG. 3A): A simple approach would be using the Fast EIT approach where the system updates the baseline values at every frame. However, this contact localization only lasts for a short amount of time (<0~3 s) for piezoresistive materials as shown in FIG. 3A. The reason is that, if the baseline keeps refreshing every frame, the changes in voltage readings disappear once the fingertip stops creating new deformations (e.g., staying at the same location).

Contact Switch (FIG. 3B): From the observations on the Fast EIT, a fingertip contact switch is needed to update the baseline properly. Once a contact is detected, the baseline stops updating and holds until the contact disappears. Thus, the contact localization remains valid even if the fingertip stays at the same location. So using the static baseline with the presence of the finger contact, we provide a robust performance on discrete contact localization. However, during a continuous fingertip movement, the residual deformations on the path continue to mark on the reconstructed images as long strokes as shown in FIG. 3B. This causes a serious problem from capturing real-time contact locations when the contacting body is in motion. In contrast to prior art methods, the presently disclosed system detects fingertip contact robustly by adding the extra capacitive sensing channel 206 within the resistance measurement loop. This extra channel 206 enables a) accurate localization regardless of the material conditions, b) real-time tracking by solely utilizing the capacitive sensing instead of looking at previous datasets such as using time-window based averaging, and c) prohibiting unintentional tracking by only taking into consideration the conductive medium such as human's body.

Contact+Movement Switches (FIG. 3C): Once the system can detect the finger movement and use it for a secondary level switch successively, real-time contact localization in continuous finger movement becomes feasible. While a fingertip remains in contact with the sensor, the system initiates updating the baseline once a movement is detected and end updating when the movement stops. This lets the system detect when to initiate and stop the baseline update under the presence of fingertip contact. Therefore, the marks from the residual deformations are erased as in FIG. 3C. In our experimental examples, it was observed that the average of all channels' instant measurements (Vavg,i) reflects a similar behavior with overall resistance distribution. To this extent, the system uses a discrete-time derivative div Vavg,i as an indicator to detect a movement. Also, the system applies a running average on div Vavg,i for a stable and robust detection (FIG. 1).

Figure 4:
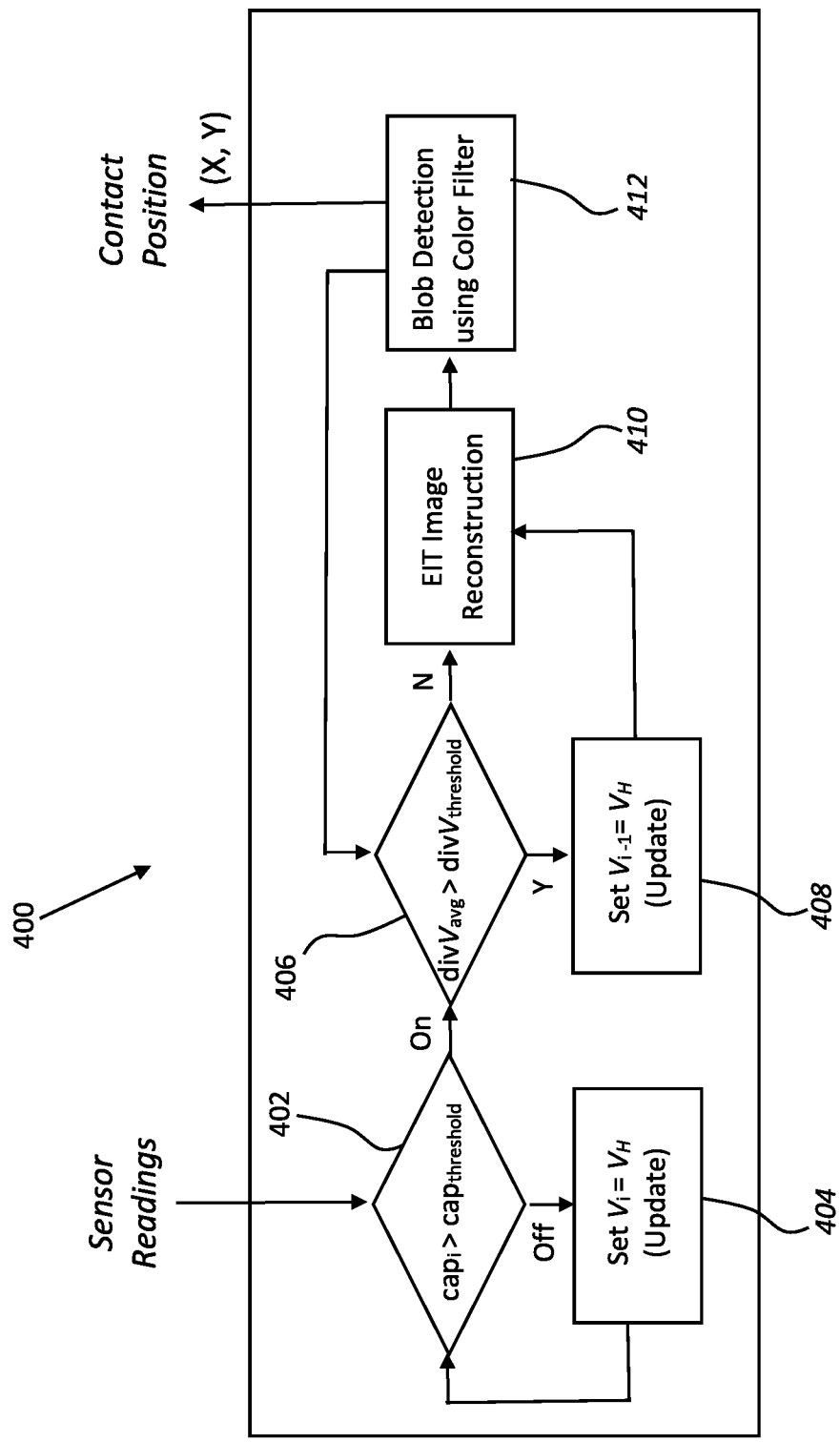
FIG. 4 is a process flowchart illustrating a touch sensing process.

By utilizing the proposed two-step event detection for the dynamic baseline updating, the presently disclosed system provides a real-time contact sensing system. FIG. 4 shows a flowchart 400 which illustrates the process. First, if a contact is not detected, i.e., the capacitive sensing value $cap_i$ is less than a predetermined threshold $cap_{threshold}$ (stage 402), instant measurement readings (Vi) are set as a homogeneous baseline data ($V_H$) (stage 404). If $cap_i >= cap_{threshold}$, a movement detection is evaluated (stage 406). If div Vavg, i>=div Vavg threshold, the system sets the previous frame's data (Vi−1) as VH (stage 408) and proceeds to perform an image reconstruction using EIT (stage 410). If div Vavg,i<div Vavg threshold, the system directly proceeds to stage 410 and performs an image reconstruction using EIT. The system may optionally apply a color filter to the reconstructed image for blob detection and localize a contact coordinate from the center of the blob (stage 412) before outputting the contact position (x, y).

Figure 5C:
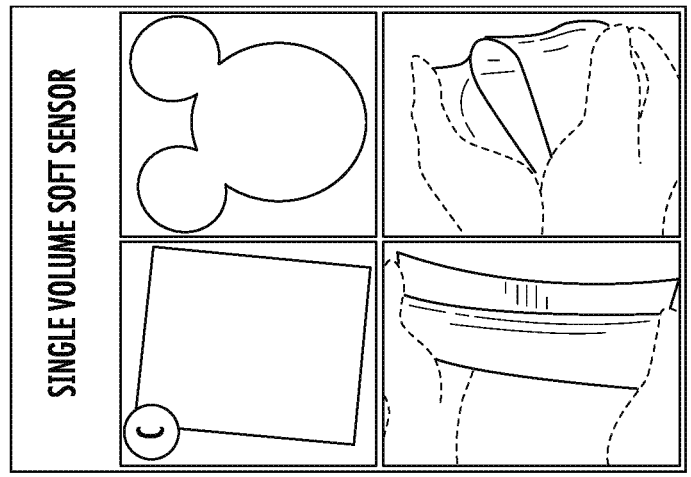
FIG. 5C shows a resulting cured sensor.
Figure 5B:
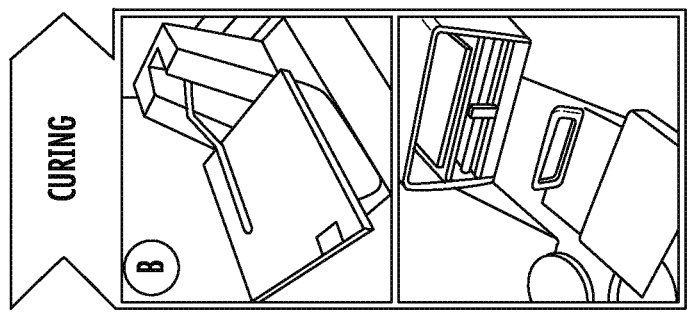
FIG. 5B shows a material curing step.
Figure 5A:
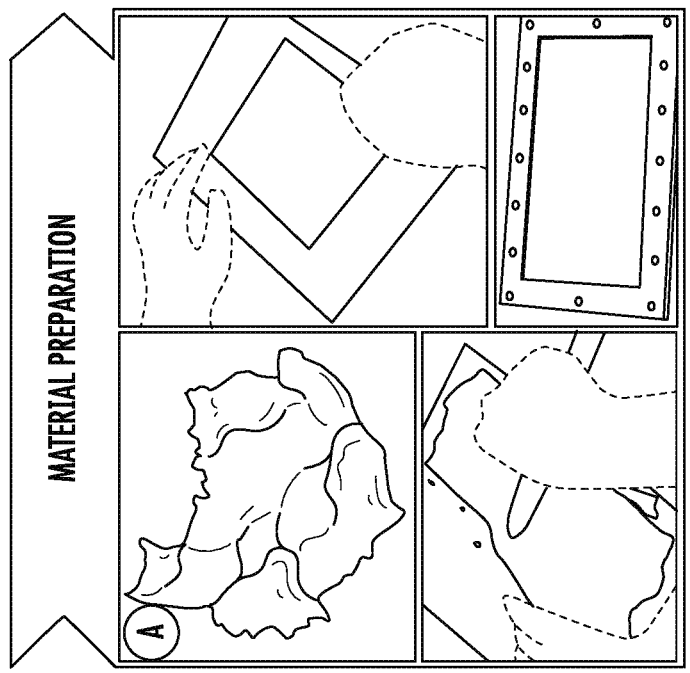
FIG. 5A shows a material preparation step.

FIGS. 5A-5C illustrate an example fabrication process for the sensor 202. As shown in FIG. 5A, the process started with applying mixed two-part components of carbon-filled elastomer to the heat stabilized film using a palette knife. Based on the size and thickness requirement, users need to adjust the volume of the elastomer. After putting another film on the other side, we used either a T-shirt heat press machine or steel blocks+oven to cure the material with constant pressure. We controlled the thickness of the material (>500 μm) by placing steel washers around the curing sample. In the illustrated example, we used a thickness of 0.8 mm, although other thicknesses may be used, for example 0.2-5 mm.

The curing takes about 140 seconds using a T-shirt heat press and 60 minutes with a toaster oven, respectively. For the T-shirt heat press, we flipped the material at 70s to apply uniform heat on both sides. It is worth noting that the material is sensitive to the curing durations where excessive durations cause Scorching. Therefore, the single volume sensor is fabricated with no additional material processing.

A customization toolkit is provided to support users in designing and deploying their own personalized interface with the disclosed system (FIG. 6). The current EIT toolkit (EIDORS) requires users to manually input geometry information and electrode locations as a set of coordinates. Using the toolkit, users can simply draw/import their own designs. Then the toolkit interfaces with the EIDORS by exporting boundary and electrode information. Lastly, it is critical to place electrodes in accordance with the simulation model since small discrepancies increase the error. Thus, the toolkit generates a guidance image that users can refer to in designing the sensor and deploying electrodes. FIG. 6A shows the overall toolkit interface, FIG. 6B shows an example interface customization, FIG. 6C shows electrode placement on the toolkit, FIG. 6D shows a guidance template, and FIG. 6E shows the finished prototype.

Figures 7A, 7B:
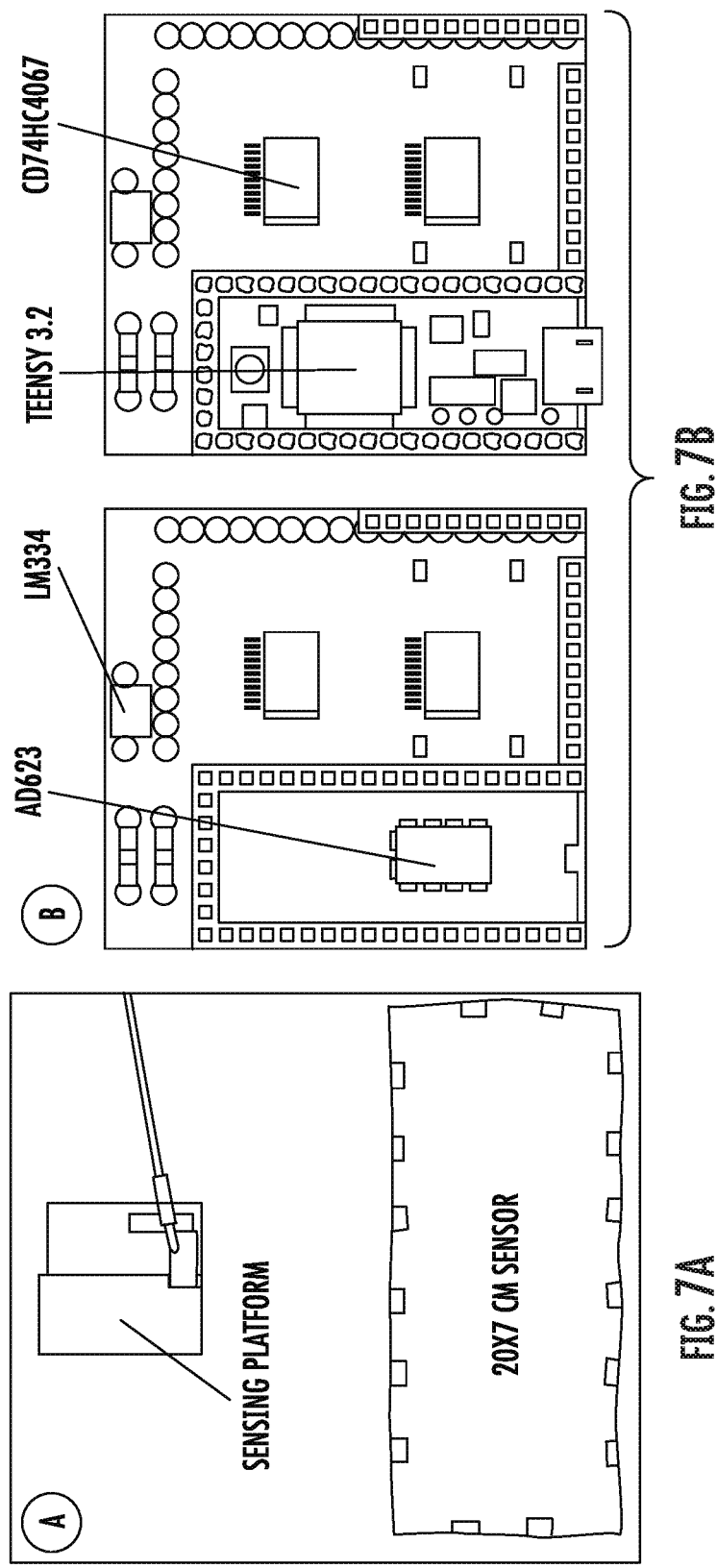
FIG. 7A shows an EIT sensing board.
FIG. 7B shows a customized 16-channel shield.

With regard to placement of the electrodes 204 on the sensor 202, there are two main factors to consider: 1) Placing electrodes with equal distances on the boundary of the given shape and 2) Avoiding sharp corners when placing the electrodes. First, not enclosing the whole sensor area shows unbalanced performance in localization among the different regions compared to the electrode placement while enclosing all the area (FIGS. 7A, 7B)). We maintain equal distance between electrodes to guarantee enclosing all the sensing regions. Second, we avoided the sharp corners since they create singularity problems due to the Neumann boundary condition used in finite element analysis of the EIT. In addition, we prevent situations where users could not place the electrodes properly (could not make full contacts or put electrodes in the designated locations) as shown in FIG. 7C. Thus, we design our customization toolkit to produce an electrode configuration that works with the EIT software toolkit, which will be discussed below. To fulfill the two aforementioned requirements namely (a) and (b), the following process may be used to determine placement of the sensors 204 as follows:

Initial electrode placement: All the points on a boundary curve are parameterized using arc length parameterization. Based on this parameterization, with a random chosen starting point, N evenly distributed electrode locations are generated in the parametric domain. The electrode number N is determined by the effective area for the interaction. In our test, we set N to be either 8 or 16. This initial electrode placement guarantees the even distribution of all electrodes.

Best electrode placement search: Based on the results of the initial electrode placement, a search algorithm is applied to find the best electrode placement that also avoids placing the electrode onto the sharp corners on the boundary curve. The evaluation metric for the sharp corners is defined as follows:

$$\text{Score} = \sum_{i=1}^{N} \overline{\text{chordal}(\Psi_{P_i})}, \quad (1)$$

where Pi is each electrode location, Pi is the set storing neighboring points of Pi, and chordal ( . . . ) measures the average chordal length error of a points in ψPi. The number of Pi's neighbors to be added in ψPi is determined with a width w·1, where 1 is the ribbon end size, and w is a user specified factor. In all our experimental tests, w is set to be 2.0. The search algorithm is designed to find a set of electrode locations with a minimum score evaluated by Eq. 1. By rotating the boundary of curve at every small step δ in the parametric domain, we recursively parameterize the same boundary curve and evaluate the score to find the best electrode locations. Note that, the searching stops when the rotation reaches 2π/N degrees due to the rotational symmetry of the electrode locations. The rotation step angle δ is set to 0.04 π/N for balancing the search resolution and the speed.

Implementation: Once the sensor fabrication was done, electrodes are installed on the periphery of the sensor to perform EIT sensing. Among the various available materials, we chose Ribbon Crimp Ends used in jewelry craft. These provided a firm contact with the sensor and easy installation/detachment. The wires were soldered onto the ribbon ends and provide connections between the sensor and the sensing board.

Figure 8:
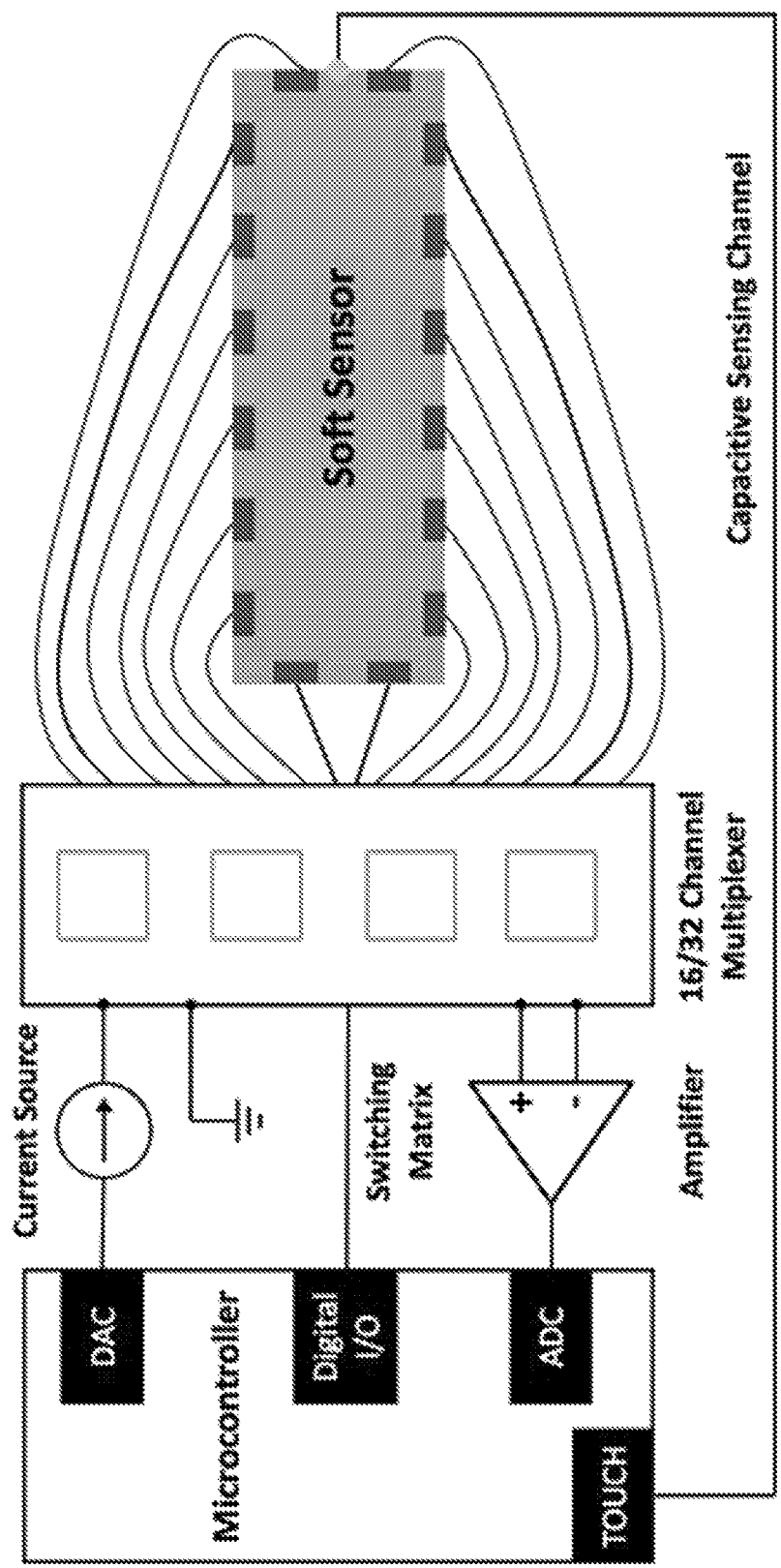
FIG. 8 shows a schematic view of a 16-electrode system.

FIG. 8 illustrates the schematic view of an example prototype according to one embodiment. The sampling was done in two steps: voltage measurements and capacitive sensing. The voltage measurements were amplified to maximize the dynamic range of the ADC reading. Microcontroller's ADC provides a 12-bit resolution and we modified ADC sampling setting to maximize the frame rate. When we injected the fixed current (<0.5 mA), we put 100 ms delay providing sufficient time for the current to propagate before starting the voltage measurements. We averaged 10 analog readings for a single voltage measurement (3 ms). At the end of the voltage reading cycle, we disabled all multiplexer channels and performed capacitive touch sensing through designated pin (Touch-Pin) in microcontroller. We modified the current, number of scans, and prescaler setting of the capacitive sensing to minimize the measurement time (<100 ms). The overall frame rate for the different number of electrodes (8, 16, and 32) along with the capacitive sensing were investigated. To test the 32 channels, we used a customized 32-channel shield with four 32-to-1 multiplexers (ADG732, Analog Devices). We observed a low frame rate (13 Hz) using 32 channels. Since we are interested in real-time contact sensing, we focus on 8 and 16 electrodes.

A For the stretching sensing, a regression analysis is employed to model the sensor behaviors upon stretching. We chose the average value from all channels (Vi) as a dependent variable since stretching the material changed the resistance distribution over the sensor area. Since the stretching sensing is a model based approach, the frame rate is like the sampling frame rate (>50 Hz).

Example Applications

Customizable 2D Soft Sensor Accessory

Figure 9C:
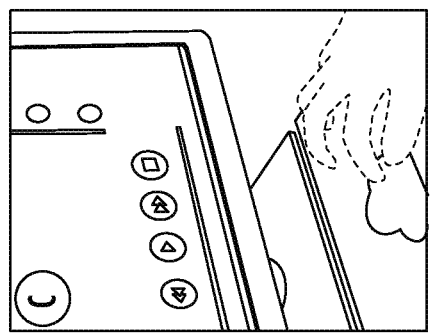
FIG. 9C shows an example interface in use.
Figure 9B:
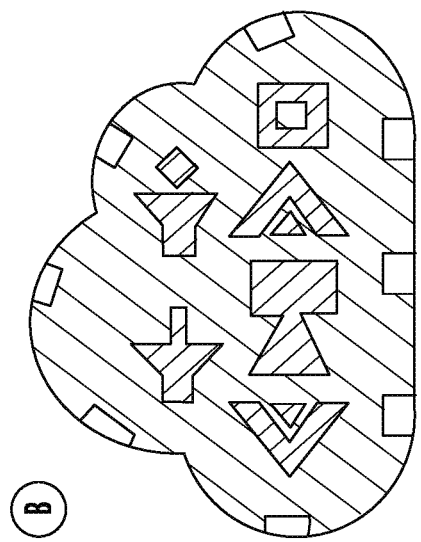
FIG. 9B shows the a sensor assembled.
Figure 9A:
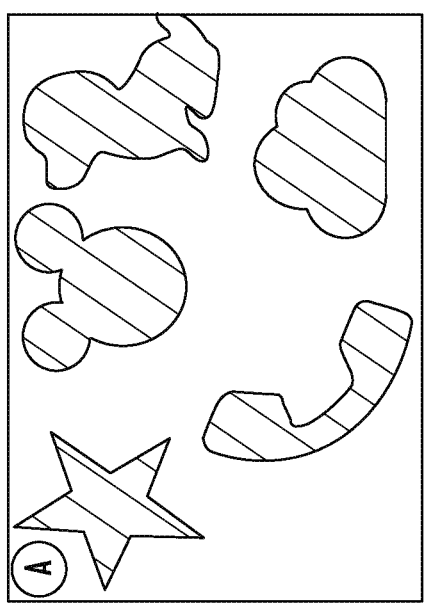
FIG. 9A shows example sensors for a personalized sensor cutouts.

A user can cut various shapes from a fabricated sheet and color them with paint markers to create customized soft sensors (FIGS. 9A-9C). These sensors can be used as controllers for various digital devices. The sensors work instantly with discrete/continuous contact sensing capability.

Interactive Lamp Arm

Figure 10C:
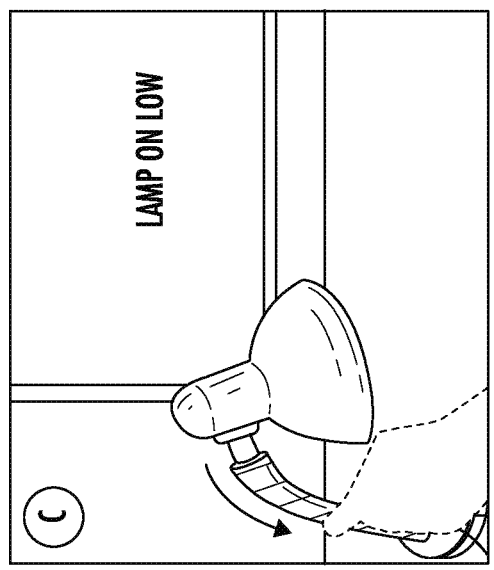
FIG. 10C shows the sensor being activated from a further position.
Figure 10B:
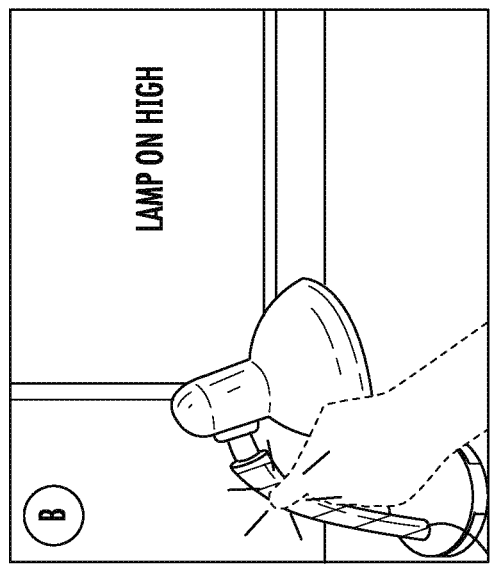
FIG. 10B shows the sensor being activated on the lamp arm.
Figure 10A:
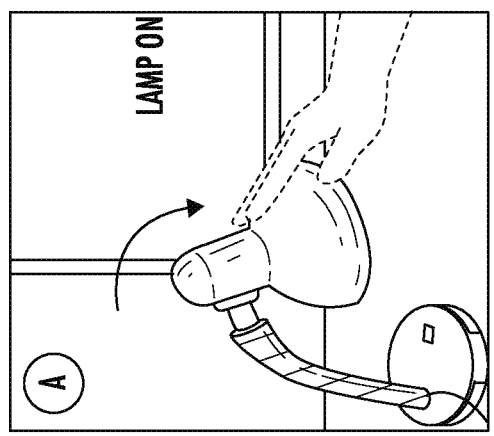
FIG. 10A shows a sensor in use on a lamp arm.

A 15×6 cm sensor was wrapped on to an adjustable lamp arm (FIGS. 10A-10C) with 8-electrode configuration. The arm of the lamp became capable of sensing bending, discrete contact, and swiping. In this example, users simply turned on the lamp by bending the arm and controlled the brightness using different arm locations.

Add-on Interactive Sticker for a Tumbler

Using the sensor and the toolkit, users can build their own soft interface for a Tumbler (FIGS. 11A-11C). Users can customize interfaces and the toolkit automatically generates the interface layout onto a 2D rectangular pattern, and creates a guide for users to build a soft sensor sticker. The fabricated sensor can be attached onto the cup with adhesives and the tumbler instantly turns into a personalized music controller.

Smart Textile Controller

Textile sensors may be fabricated and decorated with fabric transfer paper and paint markers (FIGS. 12A-12C). The sensor can be attached either outside or inside, and a user can use the smart textile as a wearable controller. Various parts of clothing can become interactive such as sleeves and pockets.

Neck Pillow TV Control

The sensor can be attached or embedded with a volumetric fabric such as neck pillow (FIGS. 13A and 13B). In this example, a user can control the channel by pressing different parts of the pillow and the volume by pressing+stretching different sides of the pillow. This demonstrates the use of the multimodal sensing capability utilizing a user's natural motions. A user can also stretch the pillow longer for faster volume change.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 14:
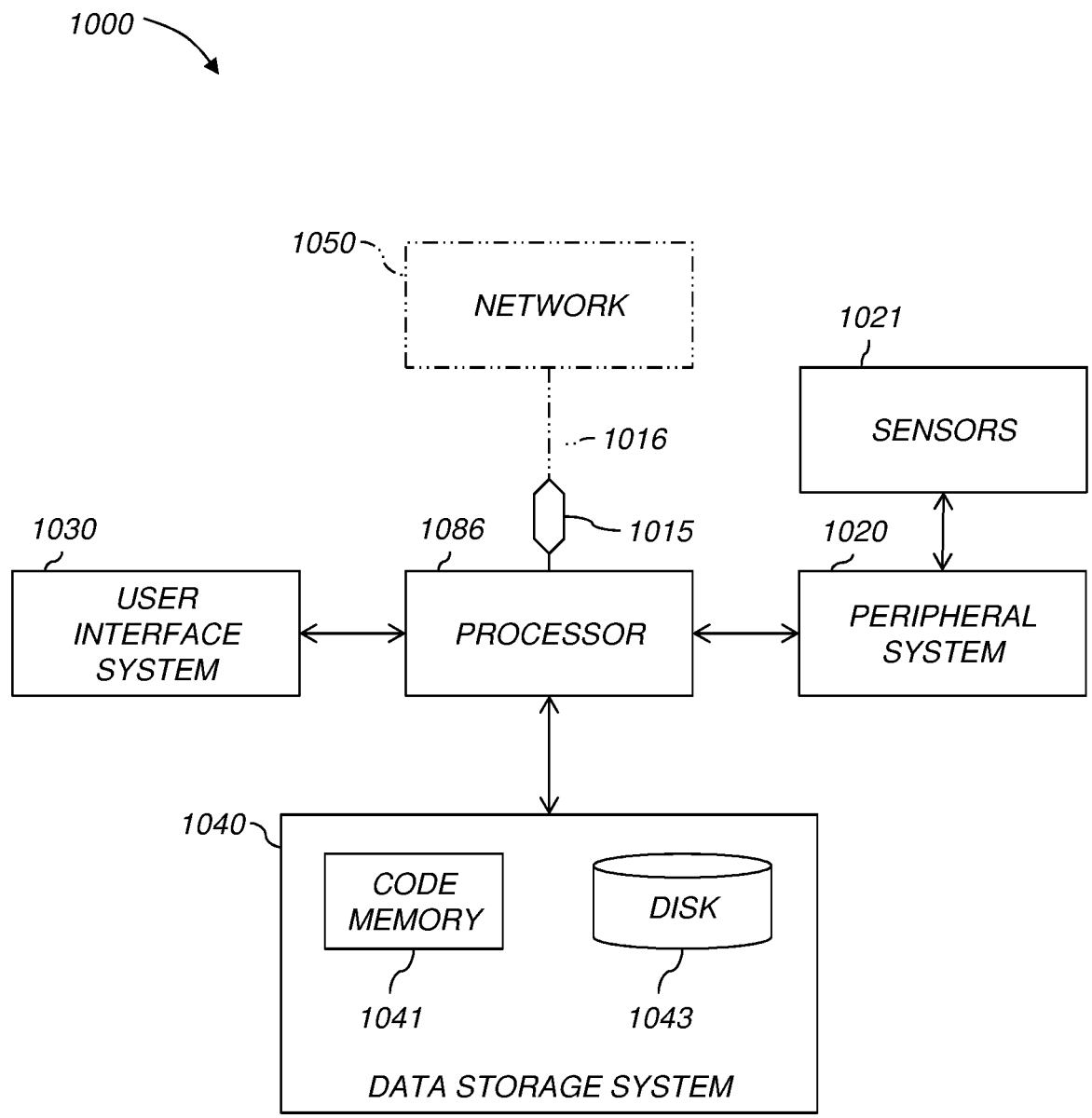
FIG. 14 illustrates a high-level diagram showing the components of a sensing system.

FIG. 14 is a high-level diagram showing the components of the exemplary system 1000 for analyzing the EIT location data and performing other analyses described herein, and related components. The system 1000 includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The EIT data may be received using sensor 202 (via electrodes 204) and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Those skilled in the art will recognize that numerous modifications can be made to the specific implementations described above. The implementations should not be limited to the particular limitations described. Other implementations may be possible.

What is claimed is:

1. A sensing system, comprising:
a stretchable base material which changes its resistance distribution upon mechanical deformation;
a plurality of electrodes attached to a perimeter of the base material;
a capacitive sensing channel attached to the base material;
a control unit operatively connected to the plurality of electrodes and the capacitive sensing channel, the control unit configured to utilize electrical impedance tomography to estimate changes of resistance distribution on the sensing system caused by a human body contact to determine a reconstructed image of a location and shape of the human body contact; and
wherein the control unit is further configured to begin adaptively updating a baseline electrical impedance tomography (EIT) measurement when the human body contact with the base material begins and stop updating the baseline EIT measurement when the human body contact with the base material ends.

2. The sensing system of claim 1, wherein said human body contact beginning and ending are sensed by the control unit via the capacitive sensing channel.

3. The sensing system of claim 1, wherein the base material comprises a carbon filled elastomer.

4. The sensing system of claim 1, wherein the control unit utilizes a neighboring method to sense the location and shape of said human body contact, said neighboring method comprising:
measuring a first voltage differential between a first adjacent pair of the plurality of electrodes;
measuring a second voltage differential between a second adjacent pair of the plurality of electrodes, the first and second adjacent pairs of the plurality of electrodes having a common electrode; and
continuing to measure voltage differentials between further adjacent pairs of the plurality of electrodes until all adjacent pairs of the plurality of electrodes have been evaluated for their voltage differential.

5. The sensing system of claim 4 wherein the control unit is further configured to:
measure a baseline measurement of said voltage differentials; and
determine when the base material has been mechanically stretched based on differences in said voltage differentials.

6. The sensing system of claim 1, wherein the control unit is further configured to apply a color filter to the reconstructed image to localize a contact coordinate from a center of the image.

7. The sensing system of claim 1, wherein the base material is imprinted with graphics to indicate control buttons of a device user control interface.

8. The sensing system of claim 1, wherein the electrodes are evenly spaced along the perimeter of the base material.

9. The sensing system of claim 1, further comprising a current source connected between the control unit and the electrodes.

10. The sensing system of claim 1, further comprising an amplifier connected in a return path from the electrodes to the control unit.

11. A sensing system, comprising:
a stretchable base material which changes its resistance distribution upon mechanical deformation;
a plurality of electrodes attached to a perimeter of the base material;
a capacitive sensing channel attached to the base material;
a control unit operatively connected to the plurality of electrodes and the capacitive sensing channel, the control unit configured to utilize electrical impedance tomography to estimate changes of resistance distribution on the sensing system caused by a human body contact to determine a reconstructed image of a location and shape of the human body contact; and wherein the control unit is further configured to apply a color filter to the reconstructed image to localize a contact coordinate from a center of the image.

12. The sensing system of claim 11, wherein the base material comprises a carbon filled elastomer.

13. The sensing system of claim 11, wherein the control unit utilizes a neighboring method to sense the location and shape of said human body contact, said neighboring method comprising:

measuring a first voltage differential between a first adjacent pair of the plurality of electrodes;

measuring a second voltage differential between a second adjacent pair of the plurality of electrodes, the first and second adjacent pairs of the plurality of electrodes having a common electrode; and continuing to measure voltage differentials between further adjacent pairs of the plurality of electrodes until all adjacent pairs of the plurality of electrodes have been evaluated for their voltage differential.

14. The sensing system of claim 13, wherein the control unit is further configured to:

measure a baseline measurement of said voltage differentials; and determine when the base material has been mechanically stretched based on differences in said voltage differentials.

15. The sensing system of claim 11, wherein the base material is imprinted with graphics to indicate control buttons of a device user control interface.

16. The sensing system of claim 11, further comprising a current source connected between the control unit and the electrodes.

17. The sensing system of claim 11, further comprising an amplifier connected in a return path from the electrodes to the control unit.

18. A sensing system, comprising:

a stretchable base material which changes its resistance distribution upon mechanical deformation;

a plurality of electrodes attached to a perimeter of the base material;

a capacitive sensing channel attached to the base material;

a control unit operatively connected to the plurality of electrodes and the capacitive sensing channel, the control unit configured to utilize electrical impedance tomography to estimate changes of resistance distribution on the sensing system caused by a human body contact to determine a reconstructed image of a location and shape of the human body contact; and wherein the base material is imprinted with graphics to indicate control buttons of a device user control interface.

19. The sensing system of claim 18, wherein the base material comprises a carbon filled elastomer.

20. The sensing system of claim 18, wherein the control unit utilizes a neighboring method to sense the location and shape of said human body contact, said neighboring method comprising:

measuring a first voltage differential between a first adjacent pair of the plurality of electrodes;

measuring a second voltage differential between a second adjacent pair of the plurality of electrodes, the first and second adjacent pairs of the plurality of electrodes having a common electrode; and continuing to measure voltage differentials between further adjacent pairs of the plurality of electrodes until all adjacent pairs of the plurality of electrodes have been evaluated for their voltage differential.

21. The sensing system of claim 20, wherein the control unit is further configured to:

measure a baseline measurement of said voltage differentials; and determine when the base material has been mechanically stretched based on differences in said voltage differentials.

22. The sensing system of claim 18, further comprising a current source connected between the control unit and the electrodes.

23. The sensing system of claim 22, further comprising an amplifier connected in a return path from the electrodes to the control unit.

24. A sensing system, comprising:

a stretchable base material which changes its resistance distribution upon mechanical deformation;

a plurality of electrodes attached to a perimeter of the base material;

a capacitive sensing channel attached to the base material;

a control unit operatively connected to the plurality of electrodes and the capacitive sensing channel, the control unit configured to utilize electrical impedance tomography to estimate changes of resistance distribution on the sensing system caused by a human body contact to determine a reconstructed image of a location and shape of the human body contact; and a current source connected between the control unit and the electrodes.

25. The sensing system of claim 24, wherein the control unit utilizes a neighboring method to sense the location and shape of said human body contact, said neighboring method comprising:

measuring a first voltage differential between a first adjacent pair of the plurality of electrodes;

measuring a second voltage differential between a second adjacent pair of the plurality of electrodes, the first and second adjacent pairs of the plurality of electrodes having a common electrode; and continuing to measure voltage differentials between further adjacent pairs of the plurality of electrodes until all adjacent pairs of the plurality of electrodes have been evaluated for their voltage differential.

26. The sensing system of claim 25, wherein the control unit is further configured to:

measure a baseline measurement of said voltage differentials; and determine when the base material has been mechanically stretched based on differences in said voltage differentials.

27. The sensing system of claim 24, further comprising an amplifier connected in a return path from the electrodes to the control unit.

28. A sensing system, comprising:

a stretchable base material which changes its resistance distribution upon mechanical deformation;

a plurality of electrodes attached to a perimeter of the base material;

a capacitive sensing channel attached to the base material; and a control unit operatively connected to the plurality of electrodes and the capacitive sensing channel, the control unit configured to utilize electrical impedance tomography to estimate changes of resistance distribution on the sensing system caused by a human body contact to determine a reconstructed image of a location and shape of the human body contact; and an amplifier connected in a return path from the electrodes to the control unit.

29. The sensing system of claim 28, wherein the control unit utilizes a neighboring method to sense the location and shape of said human body contact, said neighboring method comprising:

measuring a first voltage differential between a first adjacent pair of the plurality of electrodes;

measuring a second voltage differential between a second adjacent pair of the plurality of electrodes, the first and second adjacent pairs of the plurality of electrodes having a common electrode; and continuing to measure voltage differentials between further adjacent pairs of the plurality of electrodes until all adjacent pairs of the plurality of electrodes have been evaluated for their voltage differential.

30. The sensing system of claim 29, wherein the control unit is further configured to:

measure a baseline measurement of said voltage differentials; and determine when the base material has been mechanically stretched based on differences in said voltage differentials.

* * * * *